United States Patent [19]

Fitton et al.

[11] 4,157,445

[45] Jun. 5, 1979

[54] METHOD FOR THE PREPARATION OF QUINOLINE AND ANILINE COMPOUNDS

[75] Inventors: Peter Fitton, Pequannock, N.J.; Edward A. Rick, Charleston, W. Va.; Kurt Weinberg, Upper Saddle River, N.J.

[73] Assignee: Union Carbide Corporation, New York, N.Y.

[21] Appl. No.: 572,323

[22] Filed: Apr. 28, 1975

[51] Int. Cl.$^2$ .................... C07D 215/04; C07C 85/11
[52] U.S. Cl. .................................. 546/181; 260/574; 260/580; 546/70; 546/81; 546/152; 252/431 P

[58] Field of Search .......................... 260/283 SY, 580; 546/181

[56] References Cited

U.S. PATENT DOCUMENTS 3,705,163  12/1972  Horvitz et al. ................ 260/283 SY Primary Examiner—Donald G. Daus
Assistant Examiner—D. B. Springer
Attorney, Agent, or Firm—Bernard Francis Crowe

[57] ABSTRACT

Quinoline and aniline compounds have been synthesized from aromatic nitro compounds and ethylenically unsaturated hydrocarbons in the presence of complexes of Group VIII metals used as catalysts.

11 Claims, No Drawings

METHOD FOR THE PREPARATION OF QUINOLINE AND ANILINE COMPOUNDS

BACKGROUND OF THE INVENTION

This invention pertains to the preparation of quinoline and aniline compounds from aromatic nitro compounds and ethylenically unsaturated hydrocarbons and more particularly to the use of catalysts based on Group VIII metal complexes which catalyze this reaction.

The synthesis of quinoline and derivatives thereof has long been of interest in the field of organic chemical synthesis because these compounds can be used for making dyes such as quinoline yellow, photosensitizing cyanine dyes, polymethine dyes and the like and pharmaceutical compounds, such as, antimalarials, local anesthetics, and amoebacides, and the like. Quinoline derivatives have also been used in the manufacture of mildew proofing agents, perfumes, and nicotinic acid.

One of the most well known methods for the preparation of quinoline is the Skraup synthesis which consists of heating a primary aromatic amine, such as, aniline with glycerol, concentrated sulphuric acid and an oxidizing agent such as nitrobenzene, ferric chloride or arsenic acid.

Another well known method is the Doebner-Miller synthesis which involves the interraction of a mole of an aromatic amine, such as, aniline with 2 moles of acetaldehyde in the presence of hydrochloric acid or zinc chloride to provide 2-methylquinoline.

The Conrad-Limpach-Knorr synthesis utilizes the condensation of a beta-keto ester, such as, ethyl acetoacetate with an aromatic amine, such as, aniline and affords 2- and 4-hydroxy quinolines.

The Pfitzinger reaction comprises the condensation of isatin with aldehydes, ketones, acids or esters to form 4-carboxy quinoline.

The Friedlander, Camps, and V. Niementokowski reactions condense an ortho-substituted aniline in a basic medium with a carbonyl compound to form the quinoline derivative.

Detailed reviews of procedures employed for the preparation of quinoline and its derivatives can be found in the Kirk-Othmer Encyclopedia of Chemical Technology, Second Edition, 1968, Vol. 16, pages 865–899, Interscience Publishers Incorporated, NYC, R. C. Elderfield's "Heterocyclic Compound", Volume 4, John Wylie and Sons, New York City—1952 and are set forth in Chemical Abstracts, Volume 52, 8140f (1958).

SUMMARY OF THE INVENTION

An improved method for the synthesis of quinoline and substituted quinolines which also produces aniline compounds has been discovered which comprises interacting:

(1) a mixture of a nitro-substituted aromatic hydrocarbon containing 6 to 18 aromatic ring carbon atoms and a replaceable hydrogen atom ortho to each nitro group with (2) an ethylenically unsaturated hydrocarbon having the formula:

$$CH_2=CH-R$$

wherein R is a monovalent radical selected from the class consisting of hydrogen, alkyl groups having 1 to about 8 carbon atoms, cycloaliphatic groups having about 5 to about 7 carbons, and aromatic groups having 6 to about 18 carbon atoms, in a molar ratio of (2) to (1) of about 1:2 to 20:1 in the presence of (3) a catalytic amount of a catalyst having the formula:

$$L_nM(X)_a(R)_b$$

wherein X is a monovalent radical, L is a ligand selected from the group consisting of triarylphosphines having 6 to 18 carbon atoms, trialkylphosphines having 1 to about 8 carbon atoms, triarylarsines, having 6 to 18 carbon atoms, triarylstibines having 6 to 18 carbon atoms, and benzonitrile, M is a metal selected from Group VIII of the Deming periodic table consisting of palladium, platinum, ruthenium, rhodium, osmium and iridium, R is a monovalent radical selected from the class consisting of aryl groups having 6 to 10 carbon atoms, either unsubstituted or substituted in the ortho, meta, or para position with halogen, nitro or cyano groups, alkaryl groups having 7 to about 11 carbon atoms or alkyl groups having 1 to about 8 carbon atoms, n is an integer having values of 1 to 4, a is an integer having values of 1 or 2 and b is an integer having values of 0 or 1, at a temperature of about 50° C. to about 300° C. for at least 0.5 hours.

DESCRIPTION OF THE INVENTION

The process of this invention is applicable to aromatic nitro compounds containing a single ring or two or more aromatic rings in which the rings are condensed or are separated but linked together in a carbon to carbon bond. These nitro compounds include nitrobenzenes, nitronaphthalenes, nitrobisphenyl compounds and polyphenyl nitro compounds. The ring carbon adjacent to each nitro group must have a replaceable hydrogen. The above compounds can be unsubstituted or substituted. In the case of the substituted aromatic nitro compounds the only limitation is that the substituents do not interfere with the reaction of the nitro compound with the ethylenically unsaturated hydrocarbon and can include such groups as alkyl, alkaryl, aryl, aryloxy, alkoxyl, hydroxyl, amino, nitrile, sulfhydryl, thioether, carboxyl, or carboxylic ester, or halogens including fluorine, chlorine, bromine and iodine. Preferred hydrocarbon substituents include alkyl groups having up to about 4 carbon atoms and aryl groups having up to about 18 carbon atoms. The most preferred substituents are hydrogen, methyl, ethyl, chlorine, bromine, iodine and alkoxy groups having up to about 4 carbon atoms.

Particularly preferred nitro substituted aromatic hydrocarbons include nitrobenzene, p-nitrotoluene, p-nitrophenetole, p-dinitrobenzene, m-dinitrobenzene, alpha-nitronaphthalene, 1,8-dinitronaphthalene and the like.

Any ethylenically unsaturated hydrocarbon having the formula $CH_2=CH-R$ can be used in the practice of this invention where R is hydrogen or a hydrocarbon including alkyl groups, cycloaliphatic groups, or aromatic groups all of which can be unsubstituted or substituted with halogen atoms or amino groups. Preferred ethylenically unsaturated hydrocarbons include ethylene, propylene, 1-butylene, 1-amylene, 1-hexene, 1-octene, isobutylene, isooctene, styrene, p-methylstyrene, p-chlorostyrene, p-aminostyrene, vinyl cyclohexane, p-methylvinylcyclohexane, and the like.

The catalysts used in the practice of this invention are co-ordination compounds which may be prepared, for example, by the oxidative addition of an aryl, alkyl or aralkyl halide, or elemental halogen or cyanogen halide to a zero valent palladium metal complex. These catalysts have a formula:

$$L_n M(X)_a(R)_b$$

wherein L, M, X, R, n, a, and b, are defined as above. The most preferred ligand represented by L is triphenylphosphine. Next in order of preference of the ligands are triphenylphosphines containing alkyl substituents having up to about 8 carbon atoms, unsubstituted triarylphosphines, such as, trinaphthyl or trianthrylphosphines and alkyl substituted derivatives thereof and trialkylphosphines, such as, trimethylphosphine, tributylphosphine, trioctylphosphine, and the like. In addition one can also used such ligands as benzonitrile, triphenylarsine and triarylstibines, such as, triphenyl- and trinaphthylstibine.

The preferred palladium metal is palladium itself followed by platinum, ruthenium, rhodium, osmium, and iridium.

The preferred monovalent radicals represented by X are Br—, I—, and —CN. One can also use Cl— and $CH_3CO_2$— if desired.

When the catalysts used in this invention contain the monovalent radical represented by R it is preferred that this entity be o- chloro, o-bromo, or o-iodophenyl, p-chloro, p-bromo or p-iodophenyl, o-nitrophenyl, o-cyanophenyl, or p-cyanophenyl. If desired R can also be any substituted or unsubstituted aryl, or arylalkyl group having about 7 to 11 carbon atoms such as naphthyl, benzyl, and the like. It is also possible to employ as the R constituent alkyl, alkenyl, or alkyl groups having up to about 8 carbon atoms as well as —CN, $CCl_3$, —COOEt, —$CH_2Cl$, —$CHCl_3$, and —$COCH_3$.

The preparation of these catalysts of Type I and II is exemplified by the following examples:

(1) Oxidative addition of p-dibromobenzene to palladium tetrakis (triphenylphosphine) which results in the formation of bromo(4-bromophenyl)bis(triphenylphosphine) palladium (II):

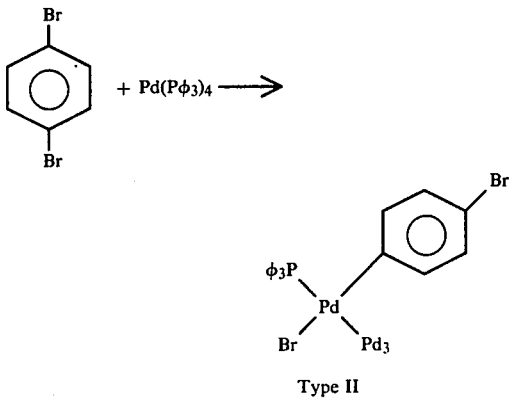

Type II (2) Oxidative addition of iodine to palladium tetrakis(triphenylphosphine)

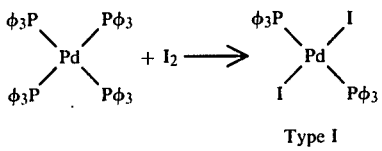

Type I (3) Replacing the ligands of compounds of Type (II) with halogens such as iodine

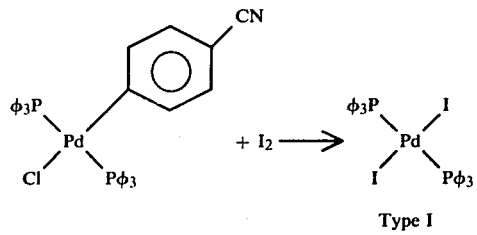

Type I (4) Reaction of potassium or sodium or ammonium tetrahalopalladates with triphenylphosphine

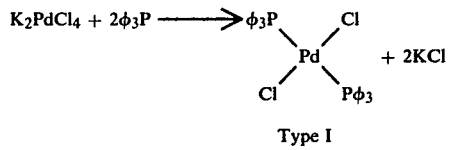

Type I

While one can use a molar ratio of ethylenically unsaturated hydrocarbon to nitro substituted aromatic hydrocarbon in the range of 1:2 to 20:1, it is preferred to use a ratio in the range of from 3:1 to 10:1.

While catalytic quantities of the catalyst of this invention can be used, it is preferred to use a mole ratio of nitro substituted aromatic hydrocarbon to catalyst in range of from 500:1 to 1:1 and even more preferred to use a range of 500:1 to 200:1.

Pressure is not narrowly critical but for the purposes of economy atmospheric pressures are preferred where possible. When using gaseous ethylenically unsaturated hydrocarbons, superatmospheric pressures up to about 10,000 psi at the reaction temperature can be used and preferably pressures in the range of from about 400 psi to 1200 psi at the reaction temperature.

Although temperatures in the range of 50° C. to 300° C. can be used, it is preferred to use a temperature range of about 140° C. to about 150° C.

While reaction times are not critical, it is preferred to use a time of about 0.5 hours to about 50 hours with a range of from about 6 hours to 20 hours being more preferred for optimum yields and efficiencies.

An unexpected advantage of this invention is the production of aniline or derivatives thereof which can be used as an intermediate for the synthesis of dyes. This process also permits the recovery of unreacted nitro-substituted aromatic hydrocarbon thus providing a high efficiency process.

The invention is further described in the Examples which follow. All parts and percentages are by weight unless otherwise specified.

EXAMPLE 1

PREPARATION OF 2-METHYLQUINOLINE

Twenty grams of nitrobenzene and 1.1 grams of iodo (4-iodophenyl) bis(triphenylphosphine)-palladium was placed in a 300 ml. stainless steel rocking autoclave. This was sealed and pressurized with ethylene to 600 psi and heated to 160° C. This temperature was maintained for 17 hours. The autoclave was then cooled and vented. After opening the vessel the reaction mixture was analyzed by gas chromatography. This analysis showed that 6.8 grams of 2-methylquinoline (54.0% efficiency) was obtained together with 0.6 grams of aniline (7.1% efficiency) and 7 grams of unreacted nitrobenzene.

Efficiency is defined as yield divided by conversion.

The preparation of the iodo (4-iodophenyl) bis(triphenylphosphine)-palladium (II) catalyst was carried out as follows:

6.6 g. of p-diiodobenzene (0.02 mole) was dissolved in 50 ml of boiling degassed benzene under argon. The solution was allowed to cool to room temperature and 6.6 g. of tetrakis(triphenylphosphine) palladium (0) (0.0074 mole) was added and the mixture refluxed under argon for 17 hours. The mixture was cooled, stripped in vacuo, and dissolved in 300 ml of methylene chloride. After filtering the solution the solvent was distilled off again. The residue was triturated with ether and the resulting crystalline substance filtered off. The yellow material, melting at 177°–182° (d), weighed 5.17 g. This material was used as catalyst. For further purification it was recrystallized from methylene chloride hexane; m.p.: 178°–183° C. (d).

EXAMPLE 2

PREPARATION OF 2-METHYLQUINOLINE

The procedure described in Example 1 was followed with the exception that 1.03 grams of palladium di(triphenylphosphine)di-iodide was used as the catalyst. Analysis by gas phase chromatography showed that the product removed from the autoclave contained 6.13 grams of 2-methylquinoline (50.0% efficiency), 2.13 grams of aniline (21.2% efficiency), and 7.7 grams of unreacted nitrobenzene.

The palladium bis(triphenylphosphine) palladium diiodide catalyst was prepared from chloro(4-cyanophenyl)bis(triphenylphosphine)palladium (II) and iodine as follows:

0.9 g. of chloro(4-cyanophenyl)bis(triphenylphosphine)palladium (II) (0.00114 mole) was dissolved in 50 ml of boiling benzene. 0.245 g. of iodine (0.00097 mole) was added to the solution which was then refluxed for one hour. Subsequently, the solvent was removed in vacuum and the remaining dark residue triturated with 12 ml. of methylene chloride. At first the residue went in solution, but soon red crystals separated which were filtered off and dried. The substance weighed 0.56 g. and melted at 248°–252° (d.). This material was used as catalyst. For analysis it was recrystallized from methylene chloridehexane or toluene.

The same material may also be prepared by dissolving palladium chloride in an excess of potassium iodide followed by reaction with triphenylphosphine in acetone. However, the yield of the product obtainable by this route is relatively low.

EXAMPLE 3

PREPARATION OF 2,6-DIMETHYLQUINOLINE

20 Grams of p-nitrotoluene and 1.1 grams of iodo (4-iodophenyl) bis(triphenylphosphine)palladium catalyst was placed in a 300 ml. stainless steel rocking autoclave. The autoclave was sealed and pressurized with ethylene to a pressure of 600 psi and heated to 162° C. This temperature was maintained for 16 hours. The autoclave was then cooled and vented. After opening the autoclave the reaction mixture was analyzed by gas chromatography. The reaction mixture contained 8.6 grams of 2,6-dimethylquinoline (88.0% efficiency), 0.61 grams of p-toluidine (7.6% efficiency), and 10 grams of unreacted p-nitrotoluene.

EXAMPLE 4

PREPARATION OF QUINOLINE

Twenty grams of nitrobenzene, 1.1 grams of iodo (4-iodophenyl) bis(triphenylphosphine)palladium catalyst and 39 grams of liquified propylene was placed in a 300 ml. stainless steel rocking autoclave and cooled to −78° C. The vessel was sealed and heated to 220° C. This temperature was maintained for 24 hours. The autoclave was then cooled and vented. The reaction mixture removed from the autoclave was analyzed by gas chromatography and found to contain 0.32 grams of quinoline (1.9% efficiency) 5.8 grams of aniline (44.0% efficiency) and 2.8 grams of unreacted nitrobenzene.

EXAMPLES 5–9

When Example 1 is repeated with the exception that the nitrobenzene reactant is replaced by α-nitronaphthalene, p-nitrophenetole, p-dinitrobenzene, m-dinitrobenzene or 1,8-dinitronaphthalene, the corresponding substituted quinolines are obtained.

EXAMPLE 10

When Example 1 is repeated with the exception that the ethylene reactant is replaced by 1-butylene, isobutylene, 1-amylene, 1-hexene or 1-octene, the corresponding substituted quinolines are obtained.

Although the invention has been described in its preferred forms with a certain degree of particularity, it is understood that the present disclosure of the preferred forms has been made only by way of example and that numerous changes made be resorted to without departing from the spirit and the scope of the invention.

What is claimed is:

1. Method of synthesizing quinoline and aniline compounds which comprises interacting (1) a mixture of a substituted aromatic hydrocarbon containing 6 to 18 aromatic ring carbon atoms, 1 or 2 nitro substituents and a replaceable hydrogen atom ortho to each nitro group with (2) an ethylenically unsaturated hydrocarbon having the formula:

$$CH_2=CH-R$$

wherein R is a monovalent radical selected from the class consisting of hydrogen, alkyl groups having 1 to about 8 carbon atoms, cycloaliphatic groups having about 5 to about 7 carbon atoms and aromatic groups having 6 to about 18 carbon atoms, in a molar ratio of (2) to (1) of about 1:2 to 20:1 in the presence of (3) a catalytic amount of a catalyst having the formula:

$$L_nM(X)_a(R)_b$$

wherein X is a monovalent radical selected from the group consisting of Br—, I—, Cl—, $CH_3COO$— and —CN, L is a ligand selected from the group consisting of triarylphosphines having 6 to 18 carbon atoms, trialkylphosphines having 1 to 8 carbon atoms, triarylarsines, having 6 to 18 carbon atoms, triaryl stibines having 6 to 18 carbon atoms and benzonitrile, M is a metal selected from Group VIII of the Deming periodic table consisting of palladium, platinum, ruthenium, rhodium, osmium, and iridium, R is a monovalent radical selected from the class consisting of aryl groups having 6 to 10 carbon atoms, either unsubstituted or substituted in the ortho, meta or para position with halogen, nitro or cyano groups, arylalkyl groups having 7 to about 11 carbon atoms, or alkyl groups having 1 to about 8 carbon atoms, n is an integer having values of 1 to 4,
a is an integer having values of 1 or 2, and
b is an integer having values of 0 or 1, at a temperature of about 50° C. to about 300° C. for at least 0.5 hours.

2. Method claimed in claim 1 wherein the nitro-substituted hydrocarbon is nitrobenzene.

3. Method claimed in claim 1 wherein the nitro-substituted hydrocarbon is p-nitrotoluene.

4. Method claimed in claim 1 wherein the ethylenically unsaturated hydrocarbon is ethylene.

5. Method claimed in claim 1 wherein the ethylenically unsaturated hydrocarbon is propylene.

6. Method claimed in claim 1 wherein the ligand L is triphenylphosphine, the halogen X is iodine, each of n and a is 2 and b is 0.

7. Method claimed in claim 1 wherein the ligand L is triphenylphosphine, n is 3, the halogen X is iodine, a is 1 and b is 0.

8. Method claimed in claim 1 wherein the metal M is platinum.

9. Method claimed in claim 1 wherein the temperature is about 140° C. to about 250° C.

10. Method of synthesizing quinoline compounds which comprises interacting:

(A) a nitro substituted aromatic hydrocarbon selected from the group consisting of nitrobenzene, p-nitrotoluene, p-nitrophenetole, p-dinitrobenzene, m-dinitrobenzene, alpha-nitronaphthalene or 1,8-dinitronaphthalene, with (B) an ethylenically unsaturated hydrocarbon selected from the group consisting of ethylene, propylene or 1-butylene, in a molar ratio of (B) to (A) of about 1:2 to 20:1 in the presence of (C) a catalytic amount of a catalyst having the formula:

$$L_nPd(X)_a(R)_b$$

wherein X is a halogen selected from the group consisting of Cl, Br or I,

L is triphenylphosphine, and
R is a group selected from the class consisting of o-chlorophenyl, o-bromophenyl, o-iodophenyl, p-chlorophenyl, p-bromophenyl, p-iodophenyl, o-nitrophenyl, o-cyanophenyl or p-cyanophenyl,
n is an integer having values of 1 to 4,
a is an integer having values of 1 or 2, and
b is an integer having values of 0 or 1, at a temperature of 5° to 300° C. for at least 0.5 hours.

11. Method claimed in claim 10 wherein the catalyst is iodo(4-iodophenyl)bis(triphenylphosphine)-palladium (II) and the nitro substituted aromatic hydrocarbon is nitrobenzene.

* * * * *